US008427150B2

(12) United States Patent
Arai

(10) Patent No.: US 8,427,150 B2
(45) Date of Patent: Apr. 23, 2013

(54) MAGNETIC RESONANCE IMAGING APPARATUS AND METHOD OF DETERMINING EXECUTION ORDER

(75) Inventor: Koichi Arai, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 326 days.

(21) Appl. No.: 13/002,206

(22) PCT Filed: Jun. 22, 2009

(86) PCT No.: PCT/JP2009/061275
§ 371 (c)(1),
(2), (4) Date: Dec. 30, 2010

(87) PCT Pub. No.: WO2010/001747
PCT Pub. Date: Jan. 7, 2010

(65) Prior Publication Data
US 2011/0105888 A1 May 5, 2011

(30) Foreign Application Priority Data

Jul. 4, 2008 (JP) ................................ 2008-175467

(51) Int. Cl.
*G01V 3/00* (2006.01)
(52) U.S. Cl.
USPC ........................................................ 324/307
(58) Field of Classification Search .......... 324/300–322; 600/407–445
See application file for complete search history.

(56) References Cited

U.S. PATENT DOCUMENTS

| 5,414,359 | A | * | 5/1995 | Mehlkopf et al. | ............. | 324/309 |
|---|---|---|---|---|---|---|
| 6,618,609 | B2 | | 9/2003 | Liu et al. | | |
| 6,759,847 | B2 | | 7/2004 | Brinker | | |
| 7,042,219 | B2 | * | 5/2006 | Biglieri et al. | ................ | 324/309 |
| 7,075,302 | B2 | | 7/2006 | Zhu | | |
| 7,078,900 | B2 | | 7/2006 | Vu | | |
| 7,135,864 | B1 | | 11/2006 | McKinnon | | |
| 7,180,291 | B2 | | 2/2007 | Chmielewski | | |
| 7,208,950 | B2 | | 4/2007 | Deimling | | |
| 7,660,619 | B2 | * | 2/2010 | Biglieri et al. | ................ | 600/410 |
| 2012/0157824 | A1 | * | 6/2012 | Bossmann et al. | ............ | 600/420 |

FOREIGN PATENT DOCUMENTS

| JP | 8-71057 | 3/1996 |
|---|---|---|
| JP | 2001-70282 | 3/2001 |
| JP | 2003-210433 | 7/2003 |
| JP | 2006-280820 | 10/2006 |
| JP | 2009-34341 | 2/2009 |

OTHER PUBLICATIONS

C. Lin et al, Integration of Scan Time Reduction Techniques with Rearranged Elliptical Centric K-space Acquisition for 3DTOF MRA at 3. OT, Proc. Intl. Soc. Mag. Reson. Med. 14, 2006.

* cited by examiner

*Primary Examiner* — Brij Shrivastav
(74) *Attorney, Agent, or Firm* — Brundidge & Stanger, P.C.

(57) ABSTRACT

It has an object to suppress reduction of an examination efficiency caused by limitation of SAR (specific absorption rate) to the minimum level in an examination that plural imaging sequences containing different imaging sequences are consecutively executed. In consideration of the time variation of time average SAR value in the overall examination, the order of executing the imaging sequences is determined so that the SAR value falls within a predetermined range and the waiting time between imaging sequences is minimum. The determination is performed by calculating a waiting time of each of all conceivable execution orders and selecting an execution order having the minimum waiting time.

15 Claims, 10 Drawing Sheets

(a)

(b)

(i)
201

(ii)
202

(ii)
203

MAGNETIC RESONANCE IMAGING APPARATUS AND METHOD OF DETERMINING EXECUTION ORDER

TECHNICAL FIELD

The present invention relates to a magnetic resonance imaging (hereinafter referred to as "MRI") apparatus for measuring a nuclear magnetic resonance (hereinafter referred to as "NMR") signal from hydrogen, phosphorus or the like in an examinee and imaging a density distribution, a relaxation time distribution, etc. of nucleus, and particularly to a technique of enhancing an examination efficiency under limited SAR (Specific Absorption Rate).

BACKGROUND ART

The MRI apparatus is an apparatus for measuring an NMR signal generated by atomic nucleus spins constituting an examinee, particularly a tissue of a human body, and two-dimensionally or three-dimensionally imaging the shapes or functions of a head portion, an abdominal part, four limbs, etc. of the examinee. In an imaging operation, the NMR signal is added with a phase encode which is different in accordance with a gradient magnetic field and also subjected to frequency encode, so that the NMR signal is measured as time-series data. The measured NMR signal is subjected to two-dimensional or three-dimensional Fourier transform to be reconstructed to an image.

In the MRI apparatus, a radio frequency (RF) magnetic field is irradiated to an imaging site of an examinee to obtain an NMR signal. This radio frequency heats the examinee and increases the body temperature of the trunk portion. From the viewpoint of safety, an upper limit value of an SAR value as energy which is absorbed per unit mass of a living body is determined and limited by IEC standards (IEC 60601-2-33: Particular requirements for the safety of magnetic resonance equipment for medical diagnosis) or the like.

The resonance frequency of the radio frequency magnetic field irradiated to the examinee by the MRI apparatus is proportional to the magnetostatic field intensity of the MRI apparatus. Accordingly, in the high magnetic field MRI apparatus, the limitation of the SAR value is particularly severe, and it is controlled by using a method such as optimization of sequence parameters, adjustment of RF to be irradiated, application of SAR reducing sequence while monitored on a real-time basis so that the SAR value of the examinee does not go over the regulation of IEC (see Patent Document 1, Patent Document 2, Patent Document 3, Patent Document 4, Patent Document 5, Patent Document 6, Patent Document 7, for example).

PRIOR ART DOCUMENT

Patent Document
Patent Document 1: U.S. Pat. No. 7,078,900
Patent Document 2: U.S. Pat. No. 6,759,847
Patent Document 3: U.S. Pat. No. 6,618,609
Patent Document 4: U.S. Pat. No. 7,075,302
Patent Document 5: U.S. Pat. No. 7,135,864
Patent Document 6: U.S. Pat. No. 7,180,291
Patent Document 7: U.S. Pat. No. 7,208,950

SUMMARY OF THE INVENTION

Problem to be solved by the Invention

Each of the methods described above is applied to one independent imaging sequence. That is, a state that an examinee is never exposed to radio frequency magnetic field is set as an initial state, and control is performed so as to satisfy the regulation. In general, a plurality of various imaging sequences are consecutively executed in the examination using the MRI apparatus. In such an examination, the examinee has been already exposed to radio frequency magnetic field for a predetermined time at the time point when a previous imaging sequence is finished, however, each of these methods takes no consideration into such a condition. Accordingly, when each method is directly applied, the imaging sequence to be next executed is required to be awaited until the SAR value of the previous imaging sequence is set to a value which does not affect the SAR value of the next imaging sequence after the previous imaging sequence is finished.

The waiting time between the imaging sequences varies in accordance with the aspect of the time variation of the SAR values of both the imaging sequences. Accordingly, in the examination that various plural imaging sequences are consecutively executed, when the execution order thereof is not optimized, the waiting time is increased and thus the examination efficiency is lowered.

The present invention has been implemented in view of the foregoing situation, and has an object to suppress the lowering of the examination efficiency caused by limitation of SAR to the minimum level in an examination that plural imaging sequences containing different imaging sequences are consecutively executed.

Means of Solving the Problem

According to the present invention, in consideration of the time variation of an SAR value in an overall examination, the execution order of imaging sequences is determined so that the waiting time between imaging sequences is minimum.

Specifically, an MRI apparatus according to the present invention for executing an examination including plural imaging sequences is characterized in that the plural imaging sequences contain imaging sequences having different time variations in average specific absorption rate of electromagnetic waves within a predetermined time, and the MRI apparatus includes: an execution order determining unit that determines an execution order of the plural imaging sequences so that the average specific absorption rate within the predetermined time falls within a predetermined range and the examination time is shortest; and an imaging unit that executes the plural imaging sequences according to the execution order determined by the execution order determining unit.

Furthermore, an execution order determining method for plural imaging sequences according to the present invention is characterized by including: a time variation calculating step that calculates a time variation of an average specific absorption rate of electromagnetic waves within a predetermined time in each of the plural imaging sequences by using imaging parameters; a measurement pattern extracting step that extracts all conceivable measurement patterns each of which is defined as a conceivable execution order of the plural imaging sequences; an examination time calculating step that calculates an examination time based on each of all the extracted measurement patterns when an examination is executed in the order of the measurement pattern concerned while the average specific absorption rate within the predetermined time falls within a predetermined range; and an execution order determining step that determines a measurement pattern providing the shortest examination time as an execution order on the basis of the calculated examination time of each of the measurement patterns.

Effect of the Invention

According to the present invention, in an examination that plural imaging sequences containing different imaging sequences are consecutively executed, lowering of an examination efficiency caused by limitation of SAR can be suppressed to the minimum level.

MODES FOR CARRYING OUT THE INVENTION

<<First Embodiment<<

Figure 1:
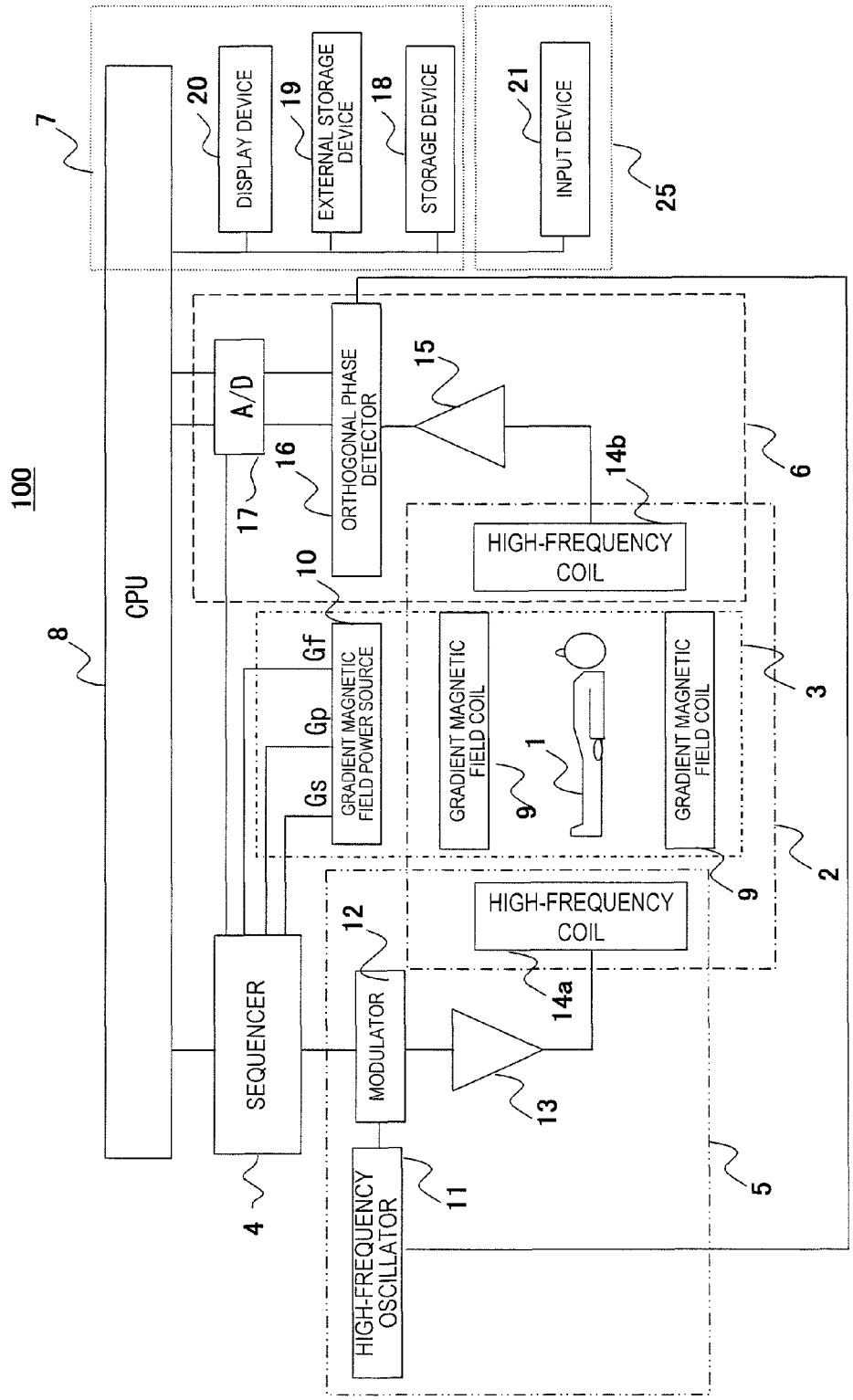
FIG. 1 is a block diagram showing the overall construction of an MRI apparatus according to a first embodiment.

A first embodiment to which the present invention is applied will be described with reference to the drawings. In all the figures to describe embodiments of the present invention, elements having the same functions are presented by the same reference numerals, and the repetitive descriptions thereof are omitted.

First, the overall construction of an MRI apparatus according to this embodiment will be described. FIG. 1 is a block diagram showing the overall construction of an MRI apparatus 100 according to the embodiment. The MRI apparatus 100 of this embodiment obtains a tomogram of an examinee by using an NMR phenomenon, and has a magnetostatic field generating system 2, a gradient magnetic field generating system 3, a transmission system 5, a reception system 6, a signal processing system 7, a sequencer 4 and a central processing unit (CPU) 8.

The magnetostatic field generating system 2 generates magnetostatic field which is uniform in a direction perpendicular to the body axis of an examinee 1 in a space surrounding the examinee 1 in the case of a vertical magnetic field type or in the body axial direction of the examinee 1 in the case of a horizontal magnetic field type. It is implemented by a magnetostatic field generating source of a permanent magnet type, a normal conduction type or a superconduction type which is disposed around the examinee 1.

The gradient magnetic field generating system 3 has gradient magnetic field coils 9 which are wound in three axial directions of X, Y and Z as the coordinate system (coordinate system at rest) of the MRI apparatus 100, and a gradient magnetic field power source 10 for driving each gradient magnetic field coil. Gradient magnetic fields Gx, Gy, Gz in the three axial directions of X, Y, Z are applied by driving the gradient magnetic field power sources 10 for the respective gradient magnetic field coils according to an instruction from the sequencer 4 described later. Under an imaging operation, a slice-direction gradient magnetic field pulse (Gs) is applied in a direction perpendicular to a slice plane (imaging cross-section) to set the slice plane for the examine 1, and a phase encode direction gradient magnetic field pulse (Gp) and a frequency encode direction gradient magnetic field pulse (Gf) are applied in the residual two directions which are perpendicular to the slice plane and also mutually perpendicular to each other, thereby encoding position information in the respective directions to echo signals.

The transmission system 5 irradiates the examinee 1 with a radio frequency magnetic field (RF) pulse to induce nuclear magnetic resonance in atomic nucleus spins of atoms constituting a living body tissue of the examinee 1, and it has a high-frequency oscillator 11, a modulator 12, a high-frequency amplifier 13 and a high-frequency coil at the transmission side (transmission coil) 14a. The RF pulse output from the high-frequency oscillator 11 is subjected to amplitude modulation by the modulator 12 at a timing instructed from the sequencer 4 described later, amplified by the high-frequency amplifier 13, and applied to the examinee 1 from the transmission coil 14a disposed in proximity to the examinee 1.

The reception system 6 detects an echo signal (NMR signal) discharged through nuclear magnetic resonance of atomic nucleus spins of atoms constituting the living body tissue of the examinee 1, and it has a high-frequency coil at the reception side (reception coil) 14b, a signal amplifier 15, an orthogonal phase detector 16 and an A/D converter 17. A response NMR signal which is induced by the RF pulse irradiated from the transmission coil 14a is detected by the reception coil 14b disposed in proximity to the examinee 1, amplified by the signal amplifier 15 and divided into orthogonal signals of two systems at a timing instructed from the sequencer 4 described later by the orthogonal phase detector 16. Each of the orthogonal signals is converted to a digital amount by the A/D converter 17, and then transmitted as measurement data to the signal processing system 7.

The sequencer 4 controls to repetitively apply an RF pulse and a gradient magnetic field pulse according to a predetermined imaging sequence, and it operates under the control of CPU 8 and transmits various instructions necessary for collection of measurement data to the transmission system 5, the gradient magnetic field generating system 3 and the reception system 6. The imaging sequence includes a time chart for defining an on/off timing of the RF pulse, the gradient magnetic field pulse, etc., an application interval (TR) of an exciting RF pulse, a band width (BW), addition frequency and a measurement condition (measurement parameters) such as a phase encode step number, etc., and defines a time variation of magnetic field acting on a measurement target under measurement by combining both the time chart and the measurement condition. The imaging sequence is created in advance according to a measurement purpose, and stored as a program and data in a storage device 18 described later or the like.

The signal processing system 7 executes various kinds of data processing and performs display, storage, etc. of processing results, and it is constructed by the CPU 8, the storage device 18 such as ROM, RAM or the like, an external storage device 19 such as an optical disk, a magnetic disk or the like and a display device 20. When measurement data are input from the reception system 6 into the CPU 8, the CPU 8 executes processing such as signal processing, image reconstruction, etc., and also it displays a tomogram of the examinee 1 on the display device 20 as a processing result and records it into the storage device 18 or the external storage device 19.

An operating unit 25 accepts an input of various kinds of control information of the MRI apparatus 100 itself and various kinds of control information of processing to be executed in the signal processing system 7, and it has a trackball or a mouse and an input device 21 such as a keyboard or the like. The operating unit 25 is disposed in proximity to the display device 20, and an operator interactively inputs information necessary for various kinds of processing of the MRI apparatus 100 through the operating unit 25 while watching the display device 20.

An imaging target nucleus type of the present MRI apparatus is hydrogen atomic nucleus (proton) which is a main constituting material of the examinee as a clinically popular material. The shape or function of a head portion, an abdominal part, four limbs or the like of a human body are two-dimensionally or three-dimensionally imaged by imaging information concerning a spatial distribution of proton density or a spatial distribution of relaxation time of an exciting state.

In FIG. 1, the transmission coil 14a and the gradient magnetic field coil 9 are disposed in the magnetostatic field space of the magnetostatic field generating system 2 in which the examinee 1 is inserted while confronting the examinee 1 in the case of the vertical magnetic field type or surrounding the examinee 1 in the case of the horizontal magnetic field type.

Furthermore, the reception coil 14b is disposed so as to confront the examinee 1 or surround the examinee 1. In this embodiment, the reception coil 14b has a surface coil for receiving an NMR signal from a measurement target area of the examinee 1 with plural coils and a whole body coil which can receive an NMR signal from the measurement target area with one coil and has a substantially uniform sensitivity distribution.

The MRI apparatus 100 according to this embodiment consecutively executes plural imaging sequences containing different imaging sequence types. In some imaging sequence types, the SAR value falls within a limited range of IEC or the like, and thus it is necessary to await the processing until the SAR value is lowered to a predetermined value after execution of an imaging sequence which has been executed just before. According to this embodiment, the execution order of the imaging sequences is determined so that the total waiting time within one examination is shortest, and the examination is executed.

In order to implement the above processing, the signal processing system 7 of the MRI apparatus 100 according to this embodiment has an execution order determining unit and an imaging unit in addition to the image reconstructing unit for executing the image reconstruction processing described above. The execution order determining unit determines the execution order of plural imaging sequences to be executed within one examination so that the total execution time is shortest within a limited SAR value range. The execution time of each imaging sequence itself is predetermined. Therefore, in this embodiment, the inclusive sum of the waiting time from the time when the just preceding imaging sequence is finished till the time when the next imaging sequence is executed is calculated, and the execution order is determined so that the inclusive sum is shortest. It is assumed that at least one imaging sequence having a different time-variation aspect of SAR is contained in the imaging sequences to be executed within one examination. The imaging unit makes the sequencer 4 execute the imaging sequences in the execution order determined by the execution order determining unit. The image reconstructing unit reconstructs an image from measurement data obtained by executing each imaging sequence.

The image reconstructing unit, the execution order determining unit and the imaging unit are implemented by loading programs stored in the storage device into the memory and executing the programs through the CPU 8. In this embodiment, these functions are implemented by executing the programs through the CPU 8 in the MRI apparatus 100, however, the present invention is not limited to this style. For example, an independent information processing device which can transmit/receive data to/from the MRI apparatus 100 may be configured so as to implement at least one of these functions and transmit only the result to the MRI apparatus 100.

The processing of the execution order determining unit of this embodiment will be described. Before description, the imaging sequence and the time variation of the SAR value will be described. With respect to the SAR value, the average value thereof within a predetermined time T (for six minutes or for ten seconds) is provided with a limitation by IEC. In the description, the average SAR value for the just-preceding time T is referred to as "time average SAR", and the regulated maximum value (limited value) is referred to as "SAR_Limit". A state that the time variation of the time average SAR is constant is referred to as "stationary state", and the maximum value of the time average SAR during execution of the imaging sequence is referred to as "SAR_Max".

Figure 2:
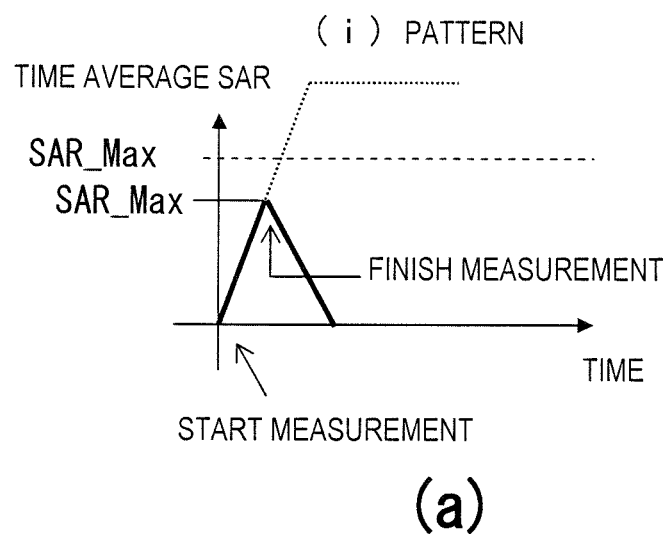
FIG. 2 is a diagram showing a pattern of the time variation of a time average SAR of imaging sequences which can be executed in a limited range of the first embodiment.
Figure 2:
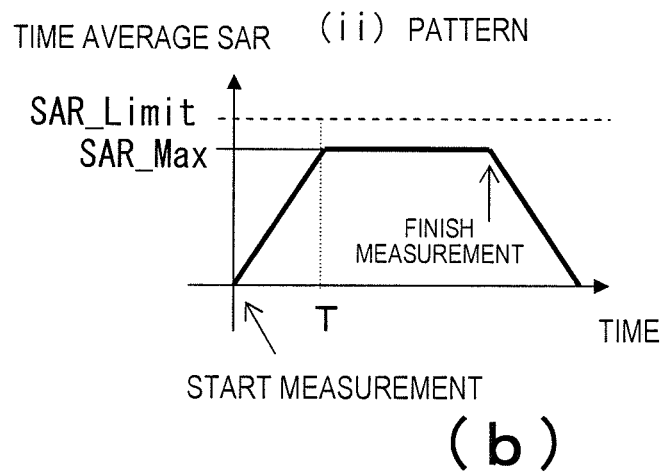

FIG. 2 shows a pattern of the time variation of a time average SAR of an imaging sequence which can be executed within such a regulation. FIG. 2(a) shows an example in which the time average SAR exceeds SAR_Limit when the time average SAR falls into a stationary state, and the imaging sequence is finished before it exceeds SAR_Limit. The pattern that the time average SAR shows the time variation as described above is referred to as (i) pattern. For example, an FSE type sequence is known as the imaging sequence in which the time variation of the time average SAR has the (i) pattern.

FIG. 2(b) shows an example in which the time average SAR does not exceed the limit value of IEC even when the time average SAR falls into the stationary state. The pattern that the time average SAR has the time variation as described above is referred to as (ii) pattern. For example, a GrE type sequence is known as the imaging sequence in which the time variation of the time average SAR has the (ii) pattern. Which one of the (i) pattern and the (ii) pattern each imaging sequence scheduled to be executed belongs to is determined at the time point when imaging parameters used in the imaging sequence concerned are input. The time variation of the time average SAR of the imaging sequence executable within the regulation is specified by the time variation pattern of any one of the (i) and (ii) patterns, the measurement time, the value of SAR_Max, etc.

Figure 3:
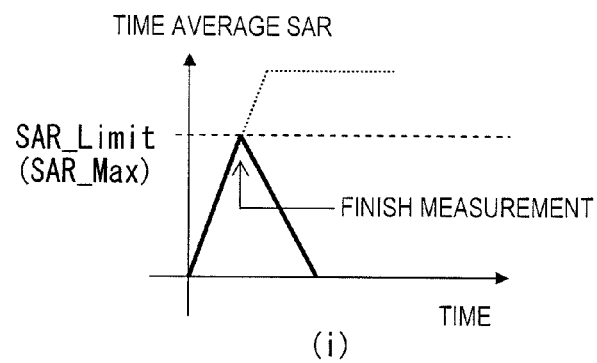
FIG. 3 is a diagram showing an example of the time variation of the time average SAR of plural imaging sequences according to the first embodiment.
Figure 3:
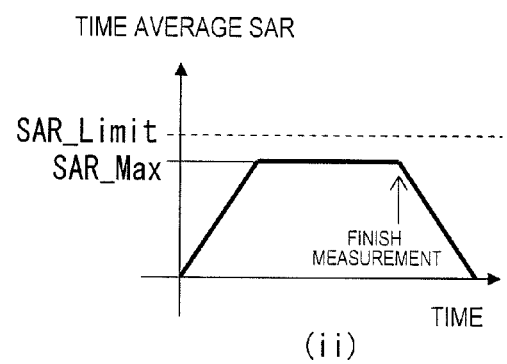
Figure 3:
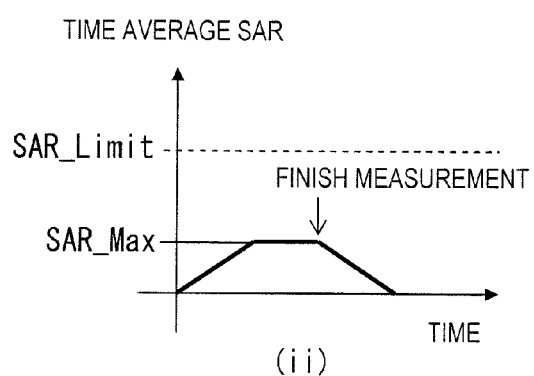

Here, an example will be described below. In this example, when plural imaging sequences having different time variations of time average SAR are executed, a waiting time occurs in accordance with the execution order of the imaging sequences. In this case, an examination including three imaging sequences is considered. FIG. 3 shows the time variation of the time average SAR of each imaging sequence. These imaging sequences are referred to as first imaging sequence 201, second imaging sequence 202 and third imaging sequence 203 respectively, and the time variation patterns of the time average SAR thereof are assumed to be set to the (i) pattern, the (ii) pattern and the (ii) pattern, respectively. In this example, it is assumed that SAR_Max of the first imaging sequence 201 is equal to SAR_Limit, and SAR_Max of the second imaging sequence 202 is larger than SAR_Max of the third imaging sequence 203.

Figure 4:
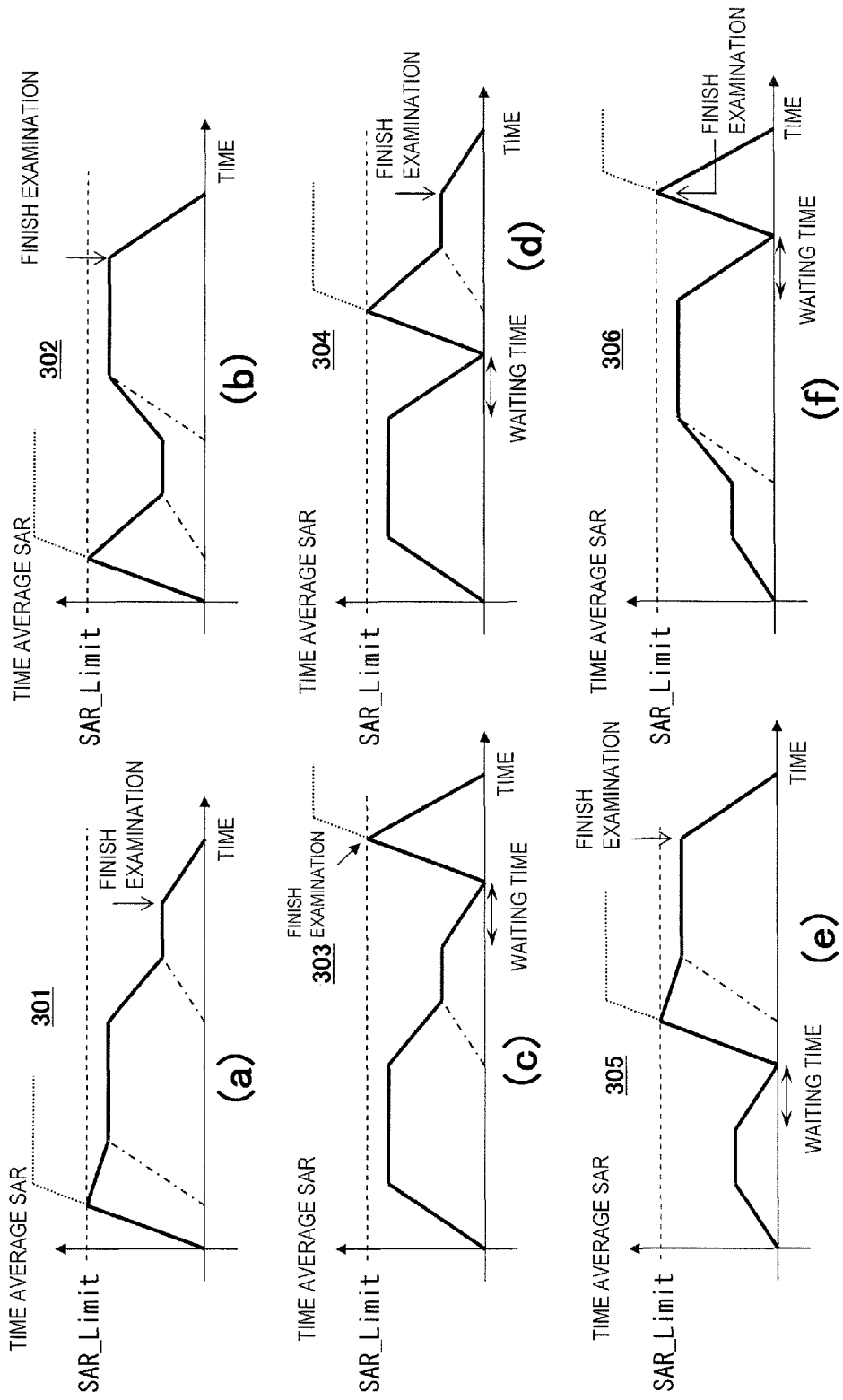
FIG. 4 is a diagram showing an example of a measurement pattern according to the first embodiment.

FIG. 4 shows execution orders of the imaging sequences which are considered in this examination (hereinafter referred to as measurement patterns). As shown in FIG. 4, six measurement patterns are considered. FIG. 4(a) shows the order of 201, 202 and 203, FIG. 4(b) shows the order of 201, 203, 202, FIG. 4(c) shows the order of 202, 203, 201, FIG. 4(d) shows the order of 202, 201, 203, FIG. 4(e) shows the order of 203, 201, 202, and FIG. 4(f) shows the order of 203, 202, 201. These orders are referred to as measurement patterns 301, 302, 303, 304, 305 and 306, respectively. In this example, as shown in FIG. 4, in the case of the measurement patterns 303, 304, 305, 306 in which the imaging sequence 201 of the (i) pattern is executed after one of the imaging sequences 202, 203 of the (ii) pattern, a waiting time is required between imaging sequences.

This reason for this is as follows. In the imaging sequences 202, 203 of the (ii) pattern of this example, the time average SAR under the stationary state is not more than SAR_Limit and is equal to SAR_Max, and thus these sequences can be started at the time point when measurement of the just preceding imaging sequence is finished. On the other hand, in the imaging sequence 201 of the (i) pattern of this example, the time average SAR under the stationary state (out of the execution time of the imaging sequence) exceeds SAR_Limit, and thus the imaging sequence must wait to start until the time point when the time average SAR at the start time of the measurement is not more than the difference between SAR_Limit and SAR_Max. In this example, SAR_Max of the imaging sequence of the (i) pattern is equal to SAR_Limit, and thus the imaging sequence is required to wait until the time average SAR of the imaging sequence which is executed just before is equal to zero.

Accordingly, in the case of the measurement patterns 303, 304, 305, 306, according to the present regulation of IEC, after the just-preceding imaging sequence is finished, the processing must wait till the start of execution of the imaging sequence 201 during T time in which the time average SAR is reduced to zero. However, in the case of the measurement patterns 301, 302, there occurs no unnecessary waiting time caused by limitation of the SAR value.

As described above, the execution order determining unit of this embodiment calculates the respective waiting times for all the measurement patterns which are conceivable for the group of imaging sequences to be executed, and a measurement pattern providing the shortest waiting time is determined as the execution order of the imaging. The execution order determination processing of the execution order determining unit according to this embodiment will be described hereunder. The time variation of the time average SAR of each imaging sequence is determined when imaging parameters are input. In this embodiment, it is assumed that a user instructs to determine an execution order after inputting imaging parameters for each imaging sequence. In this case, the number of imaging sequences to be executed is set to N (N represents natural number), and the time variations of the respective time averages SAR are assumed to be different. That is, the number of the total measurement patterns is equal to N!.

Figure 5:
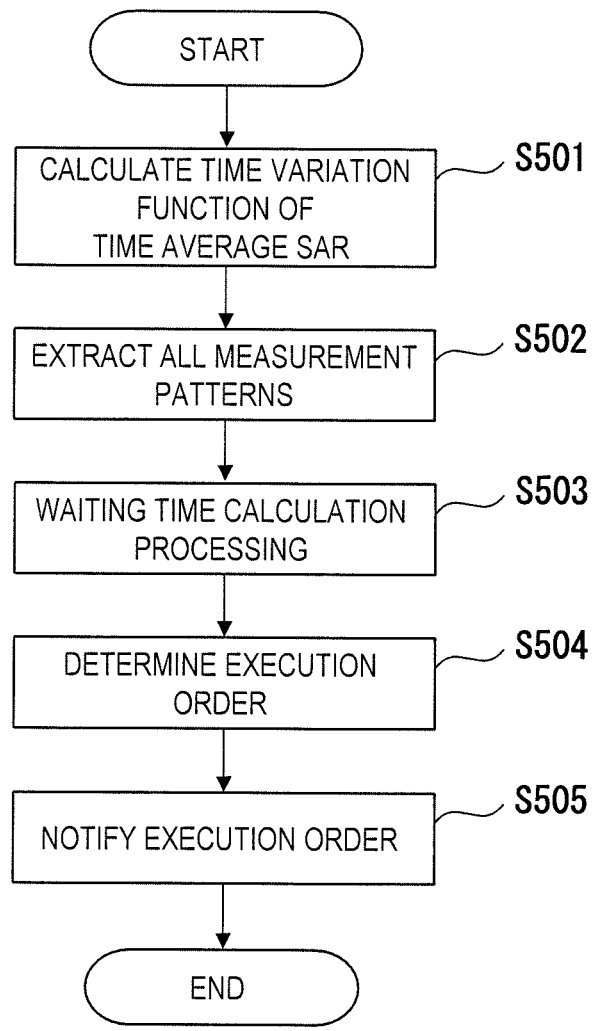
FIG. 5 is a processing flow of execution order determining processing of the first embodiment.

FIG. 5 is a processing flow of the execution order determination processing of the execution order determining unit after an instruction for determining the execution order from the user is accepted. The calculation result of each step is stored in the storage device 18.

By using input imaging parameters, the execution order determining unit calculates a function which can specify the time variation of the time average SAR with respect to each imaging sequence (step S501). Subsequently, conceivable measurement patterns (in this case, the number thereof is equal to N!) for N imaging sequences which are different in time variation of time average SAR are extracted (step S502).

With respect to all the extracted N! measurement patterns, the total waiting time corresponding to the sum of waiting times which is required for one examination is calculated (waiting time calculation processing) (step S503). A measurement pattern of which the total waiting time is shortest is determined as an execution order (step S504), the determined execution order is notified to the imaging unit (step S505), and the execution order determining processing is finished. The imaging unit executes an examination according to the notified execution order. In the execution order determination processing, with respect to the processing order of the step S501 and the step S502, any one of the steps may be executed preferentially.

Figure 6:
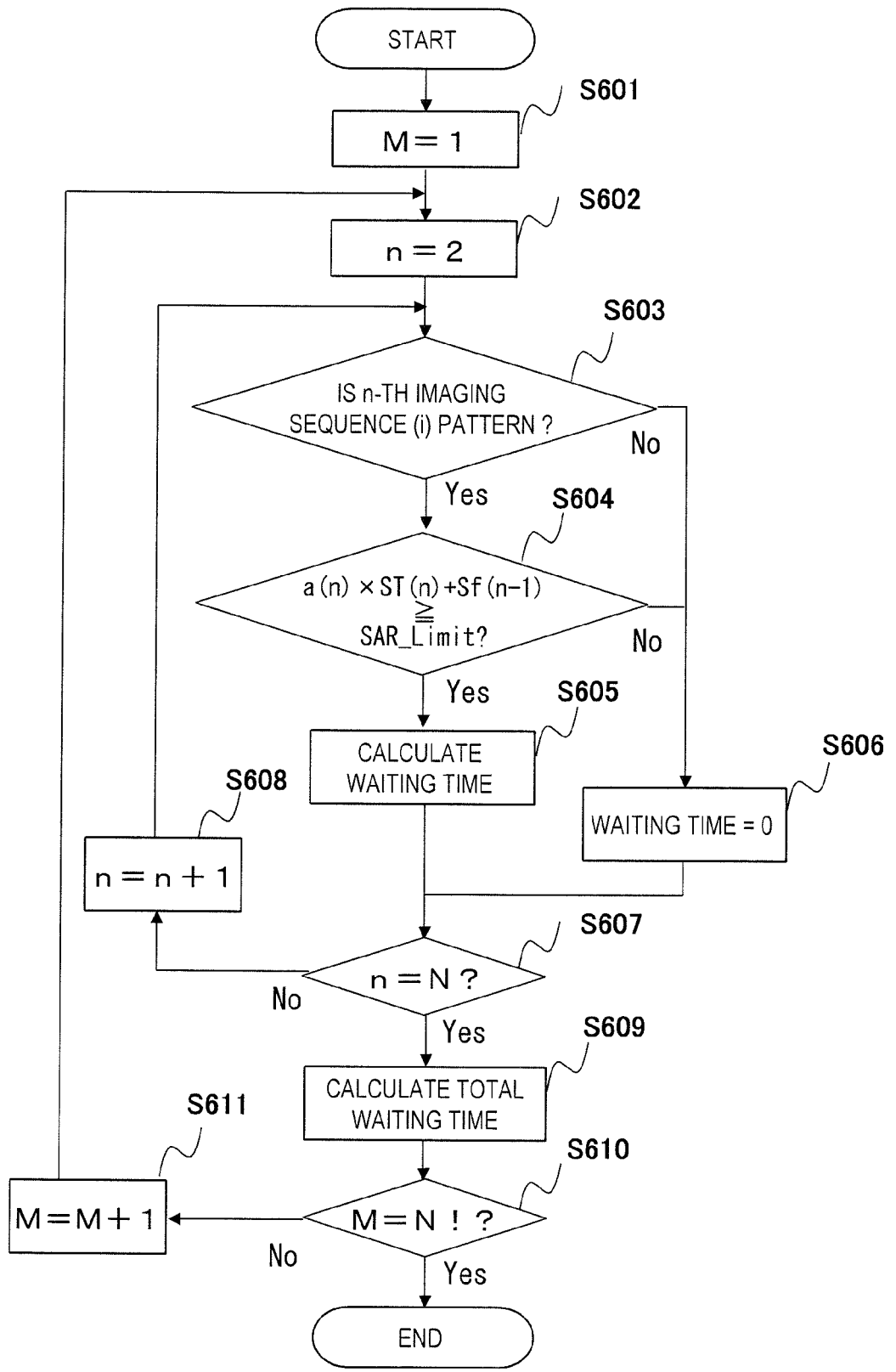
FIG. 6 is a processing flow of waiting time calculating processing of the first embodiment.

Next, the processing procedure of the waiting time calculation processing of the step S503 will be described. FIG. 6 is a processing flow of the waiting time calculation processing of this embodiment. In this case, the calculation of the total waiting time TWT in one measurement pattern is repeated at the frequency corresponding to the total measurement pattern number N!. Furthermore, the total waiting time TWT in one measurement pattern is obtained by calculating a waiting time WT(n) taken until an n-th imaging sequence is started after an (n−1)-th (n represents a natural number satisfying 2≦n≦N) imaging sequence is executed while n is calculated from 2 to N and adding the calculated waiting times.

First, the execution order determining unit substitutes 1 into a measurement pattern number counter M (step S601), and substitutes 2 into an imaging sequence counter n (step S602). The execution order determining unit determines whether the time variation pattern of the time average SAR of the n-th sequence is (i) pattern or (ii) pattern (step S603).

In a case where the time variation pattern is determined as the (i) pattern, when the n-th imaging sequence is executed just after the (n−1)-th imaging sequence is finished, it is determined whether the time average SAR exceeds SAR_Limit during the execution of the n-th imaging sequence (step S604). In this case, it is determined whether the sum of SAR_Max(n) of the time variation of the time average SAR of the n-th imaging sequence and the time average SAR at the time when the (n−1)-th imaging sequence is finished, that is, SAR_Max (n−1) exceeds SAR_Limit. Specifically, when the average SAR increasing rate of the n-th imaging sequence is represented by a (n), the measurement time of the n-th imaging sequence is represented by ST(n) and the time average SAR at the time when the (n−1)-th imaging sequence is finished is represented by Sf(n−1), it is determined whether the following mathematical expression (1) is satisfied.

$$a(n) \times ST(n) + Sf(n-1) \geqq SAR\_\text{Limit} \qquad \text{expression (1)}$$

Here, Sf(n−1) represents SAR-Max(n−1).

When the expression (1) is satisfied, a waiting time occurs. Therefore, the waiting time WT(n) is calculated according to the following mathematical expression (2) (step S605). In the following mathematical expression (2), Ss(n) represents the time average SAR at the time when the execution of the n-th imaging sequence is started.

$$WT(n) = \{Ss(n) - Sf(n-1)\} \times T / Sf(n-1) \qquad \text{expression (2)}$$

Here, Sf(n) represents SAR_Max(n).

After the waiting time WT (n) is calculated, the execution order determining unit determines whether the waiting time is calculated with respect to all the imaging sequences (n=N ?) (step S607). When the calculation has not yet been completed (n<N), n is incremented by one (step S608), and the processing returns to the step S603.

On the other hand, when the time variation pattern of the time average SAR of the n-th imaging sequence is the (ii)

pattern in step S603, the waiting time WT(n) is set to zero (step S606). Then, the processing goes to step S607. In step S604, when the result does not satisfy the mathematical expression (1), the processing shifts to step S606 to set the waiting time WT(n) to zero.

When the calculation of the waiting time WT(n) for all the imaging sequences has been finished in step S607, a total waiting time TWT is calculated as the sum of waiting times WT (n) (n=2 to N) between respective imaging sequences (step S609), and it is determined whether the processing for all the measurement patterns has been finished or not (step S610). In this case, it is determined whether M=N!. When there is some non-processed measurement pattern, the counter M is incremented by one, and then the processing returns to the step S602. On the other hand, when the processing for all the measurement patterns has been finished, the waiting time calculation processing is finished.

The execution order determining unit stores the total waiting time of each measurement pattern calculated through the waiting time calculation processing into the storage device 18 in association with each measurement pattern, and compares these total waiting times in step S504 of FIG. 5, whereby the measurement pattern providing the shortest total waiting time is determined as the execution order.

As described above, according to this embodiment, in the examination for executing plural imaging sequences containing at least one imaging sequence having a different time variation in time average SAR, the examination can be performed in an execution order which makes the waiting time shortest, that is, makes the total measurement time shortest in the regulated range of the SAR value. Accordingly, the examination can be performed in the shortest time with preserving the regulation of the SAR value, so that the efficiency of the overall examination can be enhanced.

In each embodiment, the total waiting time of each pattern is calculated to determine the execution order. However, the present invention is not limited to this style. The total measurement time may be calculated to determine the execution order. The total measurement time may be calculated by adding the total waiting time with the sum of the execution times of the respective imaging sequences.

In the above embodiment, the description is made by applying to a case where the execution order of the imaging sequences is not constrained. However, even when the execution order is constrained, the same processing can be basically performed. Here, the constraint of the execution order is such a constraint that an imaging sequence A is necessarily performed before an imaging sequence B, and an imaging sequence C and an imaging sequence D are consecutively performed in this order.

When the execution order is constrained, the number of measurement patterns extracted in the step S502 is different. For example, with respect to N imaging sequences containing imaging sequences A and B, when there is a constrained condition that the imaging sequence A is necessarily executed before the imaging sequence B, the number of extracted measurement patterns is equal to N!/2. Furthermore, when there is a constrained condition that the imaging sequence B is necessarily executed just after the imaging sequence A (the imaging sequence A and the imaging sequence B are consecutively performed in this order), the number of extracted measurement patterns is equal to (N−1)!. As described above, the execution order determining unit extracts measurement patterns on the basis of the constrained condition in step S502, and the waiting times of these measurement patterns are calculated in step S503.

Figure 7:
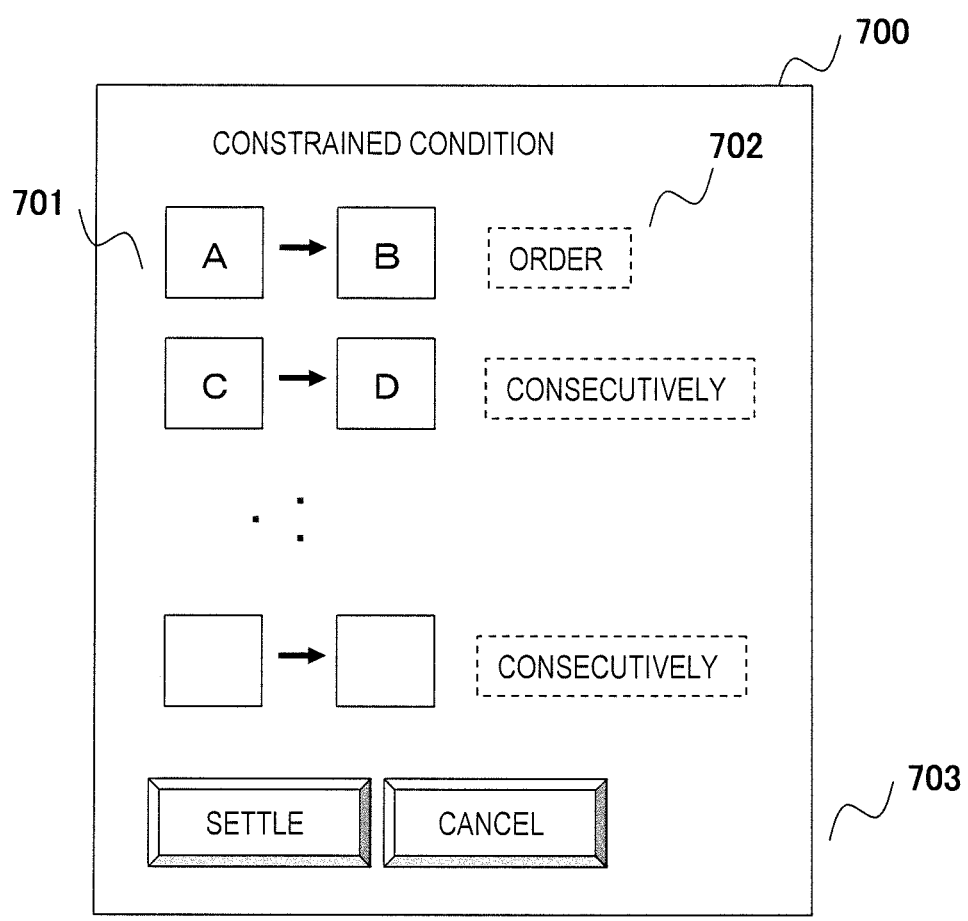
FIG. 7 is a diagram showing an example of a limiting condition input screen according to the first embodiment.

The constrained condition may be predetermined and stored in the storage device 18, or configured so as to accept an instruction from a user. In this case, an example of a screen (a constrained condition input screen 700) which is generated and displayed by the execution order determining unit is shown in FIG. 7. As shown in FIG. 7, the constrained condition input screen 700 of this embodiment has a sequence input area 701 for inputting constrained imaging sequences in the execution order by the user, a condition input area 702 for inputting a condition (whether the constraint is only a constraint concerning the order, a constraint of consecutive execution is also contained or the like), and a settling button area 703 for inputting an intention of settling or canceling an input. The execution order determining unit specifies conceivable measurement patterns according to the constrained condition input through each of the areas 701, 702 and 703.

In this embodiment, the case where all the time variations of the time average SAR of the imaging sequences to be executed are different from one another is exemplified. However, imaging sequences having time variations of the time average SAR which are perfectly identical to one another may be contained in the group of imaging sequences to be executed insofar as at least one imaging sequence having a different time variation is contained. When the imaging sequences containing the same time variation of the time average SAR are contained, the calculation frequency may be reduced in consideration in such a state when the waiting times of the respective measurement patterns are calculated in step S503.

That is, in step S501, the execution order determining unit is made to calculate a function which can specify the time variation of the time average SAR of each imaging sequence and then determine whether there are imaging sequences having the same function. When there are some imaging sequences having the same function, with respect to measurement patterns in which the imaging sequences having the same function are substituted by each other, the waiting time of any one of these measurement patterns may be calculated by the waiting time calculation processing.

Furthermore, for example when there are some imaging sequences of the (i) pattern in which SAR_Max is equal to SAR_Limit, one of these imaging sequences may be first executed certainly. This is because such an imaging sequence is required to certainly wait for the execution thereof until the time average SAR is equal to zero level. In this case, with respect to (N−1)! types of measurement patterns based on the remaining (N−1) imaging sequences, the total waiting times thereof may be calculated and compared with one another. With this construction, the processing time of the waiting time calculation processing can be shortened.

Furthermore, the execution order determined by the execution order determining unit of this embodiment is stored in the storage device 18, and when an examination including the same imaging sequence group is executed, the examination may be executed in the execution order concerned. In this case, when the same examination is executed at plural times, it is unnecessary to perform the execution order determination processing in each examination, and thus the total time of the examinations can be shortened. Furthermore, this embodiment may be configured so that with respect to a predetermined examination, the shortest execution order is calculated in another information processing device and stored in the storage device 18 in advance, and with respect to the examination concerned, the execution order calculation processing is not executed and imaging is performed according to the stored execution order.

<<Second Embodiment<<

A second embodiment to which the present invention is applied will be described. The MRI apparatus 100 of this embodiment is basically the same as the first embodiment. However, the execution order determining unit of this embodiment calculates the total waiting time of each measurement pattern of plural imaging sequences and presents it to a user. Thereafter, the execution order determining unit determines the execution order according to an instruction from the user. The imaging unit performs imaging in accordance with the determined execution order. The processing of the execution order determining unit which is different in construction from the first embodiment will be mainly described hereunder.

Figure 8:
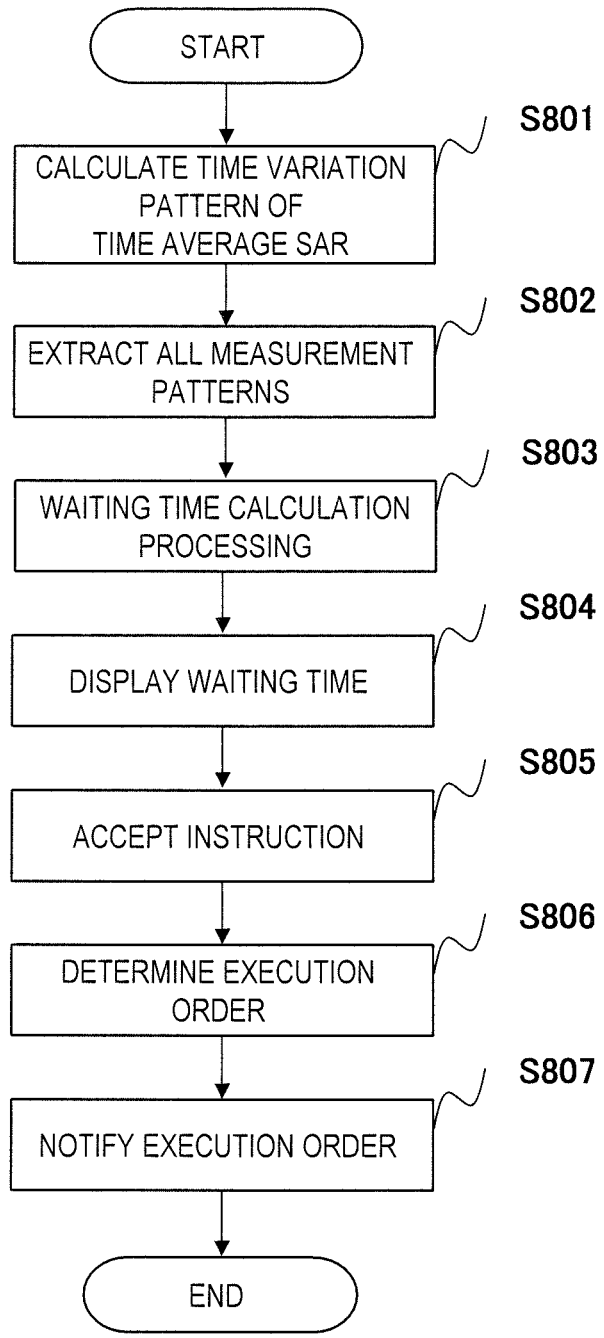
FIG. 8 is an execution order determining processing flow of a second embodiment.

FIG. 8 is an execution order determination processing flow of the execution order determining unit according to this embodiment. By using input imaging parameters, the execution order determining unit according to this embodiment calculates a function which can specify a time variation pattern of time average SAR for each imaging sequence (step S801). Subsequently, conceivable measurement patterns (in this case, N! patterns) of N imaging sequences which are different in time variation of time average SAR are extracted (step S802). With respect to all the extracted N! total measurement patterns, the total waiting times for the respective measurement patterns are calculated (waiting time calculation processing) (step S803). The waiting time calculation processing is the same as the first embodiment, and thus it is not described here. The execution order determining unit generates the obtained waiting time of each measurement pattern as a waiting time display screen and displays it on the input device 20 (step S804).

Figure 9:
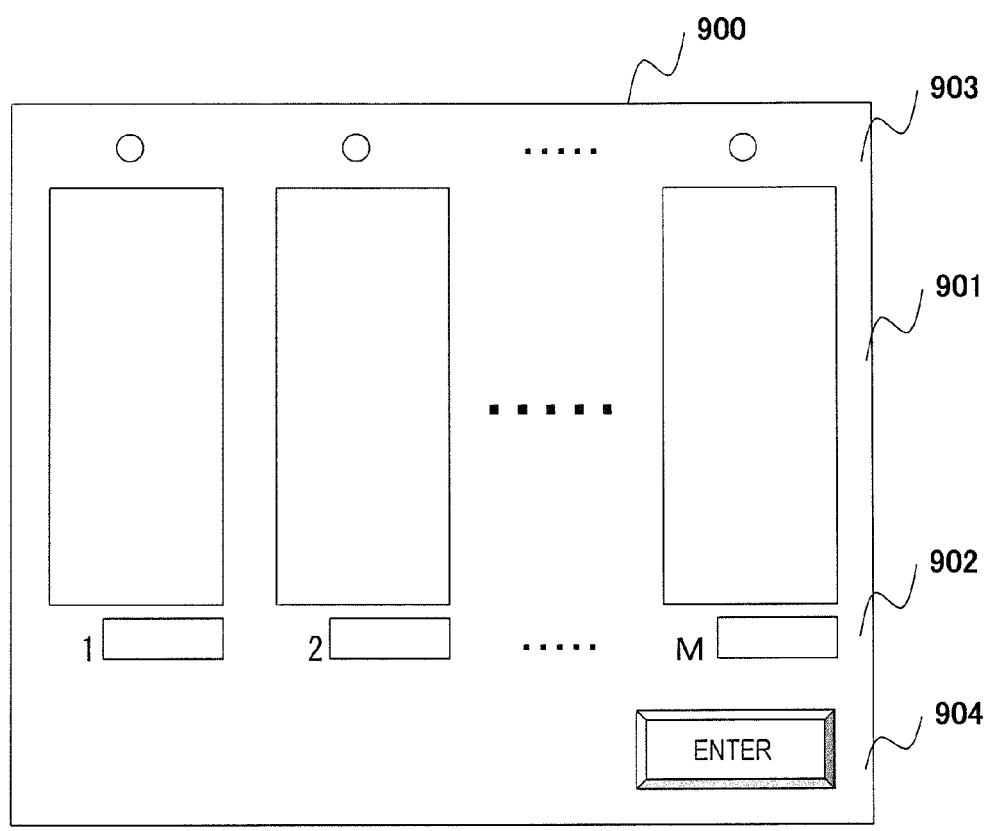
FIG. 9 is a diagram showing an example of awaiting time display screen according to the second embodiment.

Here, an example of the screen of the waiting time display screen is shown. FIG. 9 shows an example of the waiting time display screen according to this embodiment. As shown in FIG. 9, a waiting time display screen 900 of this embodiment has an order display area 901 for displaying the execution order of the imaging sequences of each measurement pattern, awaiting time display area 902 for displaying the total waiting time of each measurement pattern (N! patterns is represented by M patterns), a selection input area 903 for accepting an instruction of a measurement pattern to be adopted as an execution order from the user, and an enter button area 904 for accepting an execution order determining intention from the user. The user watches the display of the waiting time display screen 900, selects the selection input area 903 displayed at the upper portion of a desired measurement pattern by clicking or the like through the operating unit 25, and then pushes the enter button area 904 to input a decision intention.

When accepting a decision instruction from the user through the enter button area 904 of the waiting time display screen 900 (step S805), the execution order determining unit determines the measurement pattern instructed through the selection input area 903 as the execution order (step S806), notifies the determined execution order to the imaging unit (step S807), and finishes the execution order determination processing of this embodiment. The processing of the imaging unit which accepts the notification is the same as the first embodiment. Furthermore, as in the case of the first embodiment, the processing order of the step S801 and the step S802 is not limited.

As described above, according to this embodiment, the user can select a desired measurement pattern and set it as an execution order by watching the arrangement order and total waiting time of each measurement pattern. Accordingly, the user can determine the optimum execution order for the examination and perform the examination in the execution order from the comprehensive viewpoint of the execution order and total waiting time of plural imaging sequences.

In this embodiment, the total waiting times of all the measurement patterns are displayed, however, this embodiment is not limited to this style. For example, only a predetermined number J of total waiting times from the shortest waiting time may be displayed. In this case, the execution order determining unit extracts and displays measurement patterns of J having shorter total waiting times from the calculation result of the step S602.

In this embodiment, as in the case of the first embodiment, a total measurement time may be used in place of the total waiting time of one examination. Furthermore, the constrained condition may be configured to be preset or specifiable. When imaging sequences having the perfectly identical time variation of time average SAR are contained, the calculation time may be shortened in consideration of this. Furthermore, when there are some imaging sequences of the (i) pattern in which SAR_Max is equal to SAR_Limit, one of these imaging sequences may be first executed certainly. The determined execution order may be stored in the storage device 18, and used for the subsequent same examination.

<<Third Embodiment<<

Next, a third embodiment to which the present invention is applied will be described. The MRI apparatus 100 of this embodiment is basically the same as any one of the above embodiments. However, in this embodiment, the execution order determining processing is executed every time one examination sequence is executed as occasion demands, and the displacement of the time variation of the time average SAR of the just-before executed imaging sequence from an assumed value is fed back to the determination of the execution order. The processing of the execution order determining unit and the imaging unit which are different from each of the above embodiments will be mainly described. This embodiment will be described by using the first embodiment as a basis.

Figure 10:
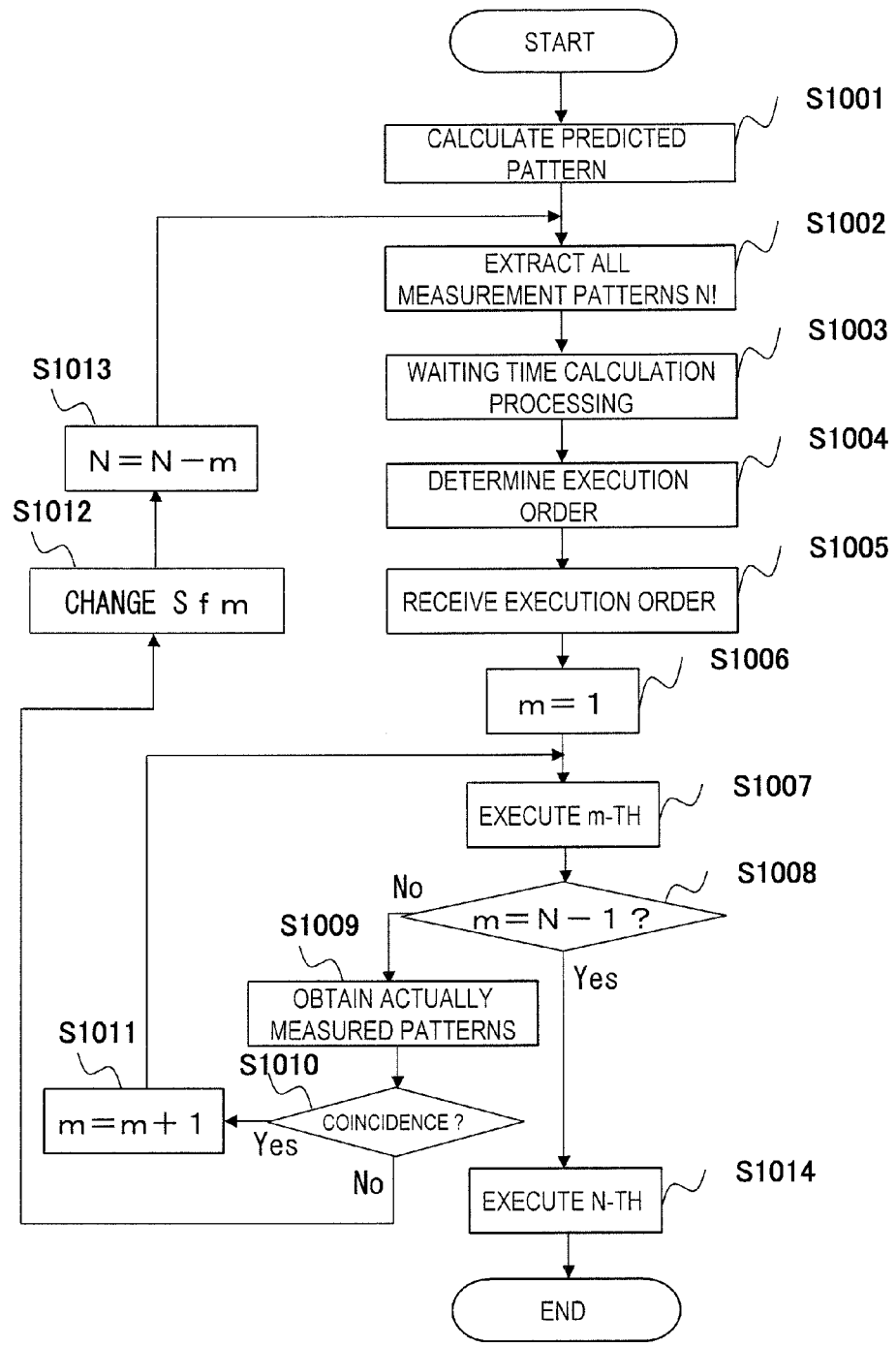
FIG. 10 is a processing flow of imaging processing according to a third embodiment.

In this embodiment, the execution order determining unit accepts an instruction from the imaging unit and executes the execution order determination processing. The processing procedure of the imaging processing of the imaging unit which contains the execution order determination processing of the execution order determining unit according to this embodiment will be described hereunder. FIG. 10 is a processing flow of the imaging processing of this embodiment.

When an input of imaging parameters and an instruction of executing imaging are accepted from the user, the imaging unit instructs the execution order determining unit to perform the execution order determination processing. Upon reception of the instruction, the execution order determining unit uses input imaging parameters to calculate a function which can specify a time variation pattern of time average SAR with respect to each imaging sequence, and stores it as a predicted pattern into the storage device 18 (step S1001). Subsequently, conceivable measurement patterns (in this case, N! patterns) of N imaging sequences having different time variation patterns of time average SAR are extracted (step S1002). With respect to all the extracted N! measurement patterns, the total waiting times thereof are calculated (waiting time calculation processing) (step S1003). The measurement pattern having the shortest total waiting time is determined as the execution order (step S1004), and the determined execution order is notified to the imaging unit (step S1005).

The imaging unit starts the examination according to the notified execution order. First, the imaging sequence counter m is set to 1 (step S1006). Then, an imaging sequence whose execution order is m-th is executed (step S1007). At this time, the time variation of the time average SAR is actually measured. When the executed imaging sequence is not the second imaging sequence from the last (m=N−1?) (step S1008), the time variation of the time average SAR of the imaging sequence concerned is obtained as an actually measured pattern (step S1009). Then, it is determined whether the actually measured pattern is coincident with a predicted pattern of the corresponding imaging sequence calculated in step S1001 (step S1010). When they are coincident with each other, m is incremented by one (step S1011), the processing returns to step S1007 to continue the examination.

On the other hand, when the actually measured pattern and the predicted pattern are not coincident with each other in step S1010, the value Sfm of the time average SAR at the time when the m-th imaging sequence is finished is changed to the actually measured value (step S1012), the number m of the imaging sequences which have been already executed is subtracted from the number N of the imaging sequences to be executed in the examination (step S1013), and the processing returns to step S1002 to set the measurement pattern having the minimum total waiting time in the remaining imaging sequence group as the execution order.

When the executed imaging sequence is the second imaging sequence from the last in step S1008, only one imaging sequence remains. Therefore, the determination based on the actual measurement as to whether the execution order is possible or impossible is not performed, the last imaging sequence (N-th imaging sequence) is executed (step S1014), and the processing is finished.

As described above, according to this embodiment, in the examination that plural imaging sequences containing at least one imaging sequence having a different time variation of time average SAR are executed, the examination can be performed in the execution order which brings the shortest waiting time, that is, the shortest total measurement time within the regulated range of the SAR value. Accordingly, the examination can be performed in the shortest time with preserving the SAR value regulation, and the efficiency of the overall examination can be enhanced. Furthermore, when the actual time variation of time average SAR is different from a predicted one, the effect of the difference therebetween can be suppressed to the minimum level.

The determination of the step S1010 may be based, not on the determination as to whether the actually measured pattern and the predicted patter are perfectly coincident with each other, but on the determination as to whether the actually measured pattern is within a predetermined range of the predicted pattern.

In this embodiment, as in the case of the first embodiment, the case where the execution order determining unit automatically determines the execution order of the measurement pattern of the shortest waiting time is exemplified. However, as in the case of the second embodiment, the user may be allowed to determine the execution order.

Furthermore, as in the case of each of the above embodiments, the total measurement time may be used in place of the total waiting time of one examination. The constrained condition may be configured to be preset or specifiable. Furthermore, when imaging sequences having the perfectly same time variation of time average SAR are contained, the calculation time may be shortened in consideration of this. Furthermore, when there are some imaging sequences of the (i) pattern in which SAR_Max is equal to SAR_Limit, one of these imaging sequences may be first executed certainly. The determined execution order may be stored in the storage device 18, and used for the subsequent same examination.

Description of Reference Numerals

1 examinee, 2 magnetostatic field generating system, gradient magnetic field generating system, 4 sequencer, 5 transmission system, 6 reception system, 7 signal processing system, 8 central processing unit (CPU), 9 gradient magnetic field coil, 10 gradient magnetic field power source, 11 high-frequency oscillator, 12 modulator, 13 high-frequency amplifier, 14a high-frequency coil (transmission coil), 14b high-frequency coil (reception coil), 15 signal amplifier, orthogonal phase detector, 17 A/D converter, 18 storage device, 19 external storage device, 20 display device, 21 input device, 25 operating unit, 700 constrained condition input screen, 701 sequence input area, 702 condition input area, 703 settling button area, 900 waiting time display screen, 901 order display area, 902 waiting time display area, 903 selection input area, 904 enter button area

The invention claimed is:

1. A magnetic resonance imaging apparatus for executing an examination comprising a plurality of imaging sequences, characterized in that the plurality of imaging sequences contain imaging sequences having different time variations in average specific absorption rate of electromagnetic waves within a predetermined time, and the magnetic resonance imaging apparatus comprises:

an execution order determining unit that determines an execution order of the plurality of imaging sequences so that the average specific absorption rate within the predetermined time falls within a predetermined range and the examination time is shortest; and an imaging unit that executes the plurality of imaging sequences according to the execution order determined by the execution order determining unit.

2. The magnetic resonance imaging apparatus according to claim 1, wherein the execution order determining unit further comprises:

a time variation calculator that calculates the time variation of the average specific absorption rate within the predetermined time with respect to each of the plurality of imaging sequences by using imaging parameters;

a measurement pattern extracting unit that extracts all conceivable measurement patterns each of which is provided as a conceivable execution order of the plurality of imaging sequences; and an examination time calculator that calculates the examination time with respect to each of all the extracted measurement patterns when the examination is executed in the order of the measurement pattern concerned while the average specific absorption rate within the predetermined time falls within a predetermined range, and a measurement pattern having the shortest examination time is determined as an execution order on the basis of the examination time of each measurement pattern calculated by the examination time calculator.

3. The magnetic resonance imaging apparatus according to claim 2, wherein the examination time calculator calculates a waiting time with respect to each of imaging sequences to be executed secondly and subsequently, the waiting time being defined as a time required from a time when a just-before imaging sequence is finished till a time when the imaging sequence concerned is started so that the average specific absorption rate within the predetermined time falls within a predetermined range, and calculates the examination time on the basis of the calculated waiting time.

4. The magnetic resonance imaging apparatus according to claim 2, further comprising:
   a display unit; and
   an input unit, wherein the execution order determining unit displays on the display unit, the examination time of each of the measurement patterns calculated by the examination time calculator, and determines a measurement pattern selected through the input unit as the execution order.

5. The magnetic resonance imaging apparatus according to claim 2, wherein the imaging unit comprises:
   a comparator that actually measures the time variation of the average specific absorption rate within the predetermined time of each imaging sequence every time each imaging sequence is executed during a process of executing the plurality of imaging sequences according to the execution order determined by the execution order determining unit, and compares the actually measured time variation with the time variation calculated by the time variation calculator; and
   an execution order re-determining unit that makes the execution order determining unit determine an execution order of non-executed imaging sequences when the difference between an actual measurement result and a calculation result is not less than a predetermined value as a comparison result of the comparator, the non-executed imaging sequences being executed in the re-determined execution order.

6. The magnetic resonance imaging apparatus according to claim 2, wherein the measurement pattern extracting unit extracts an execution order satisfying a constraint of an execution order of predetermined imaging sequences as the measurement pattern from all the conceivable execution orders.

7. The magnetic resonance imaging apparatus according to claim 6, further comprising:
   a constrained condition setting unit that accepts setting of the constrained condition.

8. The magnetic resonance imaging apparatus according to claim 2, wherein the measurement pattern extracting unit extracts, as the measurement pattern from all the conceivable execution orders, an execution order of first executing an imaging sequence in which the time variation of the average specific absorption rate within the predetermined time has a predetermined feature.

9. The magnetic resonance imaging apparatus according to claim 8, wherein the measurement pattern extracting unit extracts as the measurement pattern an execution order of first executing an imaging sequence in which the maximum value of the time variation of the average specific absorption rate within the predetermined time (SAR-MAX) is equal to a predetermined upper limit value (SAR-Limit).

10. The magnetic resonance imaging apparatus according to claim 1, further comprising:
    a storage unit that stores an execution order of the plurality of imaging sequences that is determined by the execution order determining unit,
    wherein the imaging unit executes the plurality of sequences in the execution order stored in the storage unit.

11. The magnetic resonance imaging apparatus according to claim 1, wherein the plurality of imaging sequences contain FSE type sequences and GrE type sequences.

12. A magnetic resonance imaging apparatus for executing an examination comprising a plurality of imaging sequences, the plurality of imaging sequences containing imaging sequences among which time variation of an average specific absorption rate of electromagnetic waves within a predetermined time is different, characterized by comprising:
    a storage unit that stores an execution order which is calculated in advance and determined so that an average specific absorption rate within a predetermined time falls within a predetermined range and an examination time is shortest; and
    an imaging unit that reads out the execution order stored in the storage unit and executes the plurality of imaging sequences in the execution order concerned.

13. An execution order determining method for a plurality of imaging sequences in a magnetic resonance imaging apparatus for executing an examination comprising the plurality of image sequences among which time variation of average specific absorption rate of electromagnetic waves within a predetermined time is different, characterized by comprising:
    a time variation calculating step that calculates a time variation of an average specific absorption rate of electromagnetic waves within a predetermined time in each of the plurality of imaging sequences by using imaging parameters;
    a measurement pattern extracting step that extracts all conceivable measurement patterns each of which is defined as a conceivable execution order of the plurality of imaging sequences;
    an examination time calculating step that calculates an examination time based on each of all the extracted measurement patterns when an examination is executed in the order of the measurement pattern concerned while the average specific absorption rate within the predetermined time falls within a predetermined range; and
    an execution order determining step that determines a measurement pattern providing the shortest examination time as an execution order on the basis of the calculated examination time of each of the measurement patterns.

14. The execution order determining method according to claim 13, wherein the examination time calculating step calculates a waiting time with respect to each of imaging sequences to be executed secondly and subsequently, the waiting time being calculated as a time required from a time when a just-before imaging sequence is finished till a time when the imaging sequence concerned is started so that the average specific absorption rate within the predetermined time falls within a predetermined range, and calculates the examination time on the basis of the calculated waiting time.

15. The execution order determining method according to claim 13, wherein the execution order determining step comprises:
    a display step that displays an examination time of each measurement pattern calculated in the examination time calculating step; and
    a step of accepting selection of a desired measurement pattern from the plurality of displayed measurement patterns, the selected measurement pattern being determined as the execution order.

* * * * *